United States Patent [19]

Thoman

[11] Patent Number: 4,606,328
[45] Date of Patent: Aug. 19, 1986

[54] METHOD AND APPARATUS FOR TREATING BREATHING IRREGULARITIES

[76] Inventor: Evelyn B. Thoman, 796 Stafford Rd., Storrs, Conn. 06268

[21] Appl. No.: 504,823

[22] Filed: Jun. 16, 1983

[51] Int. Cl.[4] ............................................. A61B 19/00
[52] U.S. Cl. ..................................... 128/1 C; 119/29; 446/199; 446/295
[58] Field of Search ................ 446/176, 180, 183, 184, 446/185, 197, 198, 199, 200, 202; 128/1 C; 119/29, 1; 434/262, 265, 267, 275, 295

[56] References Cited

U.S. PATENT DOCUMENTS

| | | | |
|---|---|---|---|
| 494,410 | 3/1893 | Carpenter | 446/183 |
| 536,512 | 3/1895 | Crossley et al. | 446/198 |
| 1,763,467 | 6/1930 | Klinker | 446/198 |
| 2,859,731 | 11/1958 | Sutton | 119/29 X |
| 3,125,827 | 3/1964 | Ostrander | 446/198 |
| 3,141,261 | 7/1964 | Mirando | 446/185 |
| 3,153,881 | 10/1964 | Baulard-Cogan | 446/180 |
| 3,172,223 | 8/1964 | Stager | 446/197 X |
| 3,292,611 | 12/1966 | Belkin | 128/1 C |
| 3,346,989 | 10/1967 | Ryan et al. | 446/198 |
| 3,419,923 | 1/1969 | Cowan | 128/1 C X |
| 3,563,229 | 2/1971 | Petrusson | 128/1 C |
| 4,259,805 | 4/1981 | Hornsby | 446/198 |
| 4,331,426 | 5/1982 | Sweeney | 434/265 |

FOREIGN PATENT DOCUMENTS 2650765A  5/1977  Fed. Rep. of Germany ...... 128/1 C

Primary Examiner—F. Barry Shay

[57] ABSTRACT

Vestibular and tactile responses of a living subject, human or animal, are evoked by positioning in its vicinity a simulated breathing animal, or the like as a pacifying sleeping aid. The simulated animal includes a trunk portion having a variable volume "pleural cavity". A bladder affixed to the back portion cyclically expands and contracts to simulate breathing. A pneumatic pumping system alternately increases and decreases pressure in the bladder to actuate the front or stomach of the simulated animal. Head or other apendages (arms, legs, wings and the like) may be moved by such expansion and contractions. The animal thereby produces actual movement to create a vestibular response and the covering of sheepskin or the like creates a tactile response in the living subject. In a preferred form the bladder conforms generally to the pleural cavity by filling it with an air permeable foam body with the expandable bladder loosely fitting over the foam body to suppress sound of air cyclically entering or leaving the bladder or changing position within the torso. Air from the pumping system may be heated and allowed to bleed through the bladder wall in order to warm the area around the subject.

6 Claims, 7 Drawing Figures

U.S. Patent   Aug. 19, 1986   Sheet 1 of 2   4,606,328
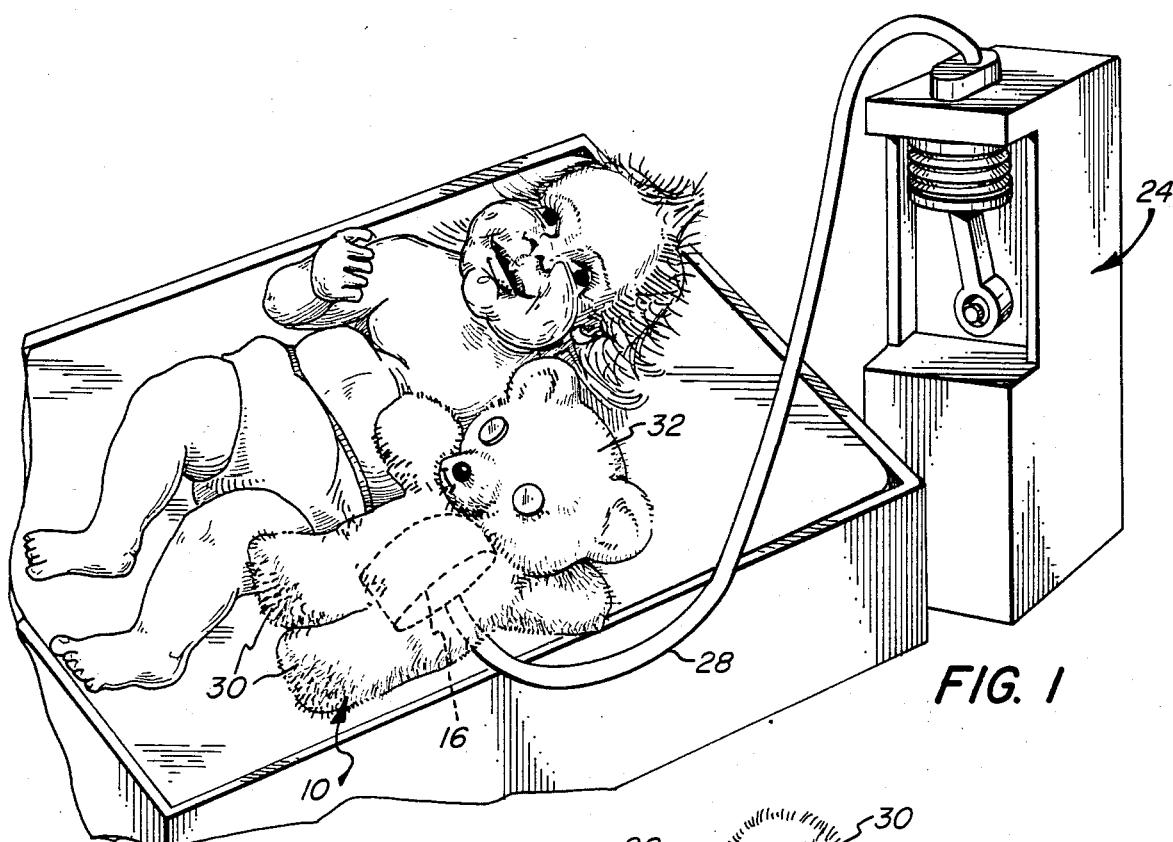
FIG. 1
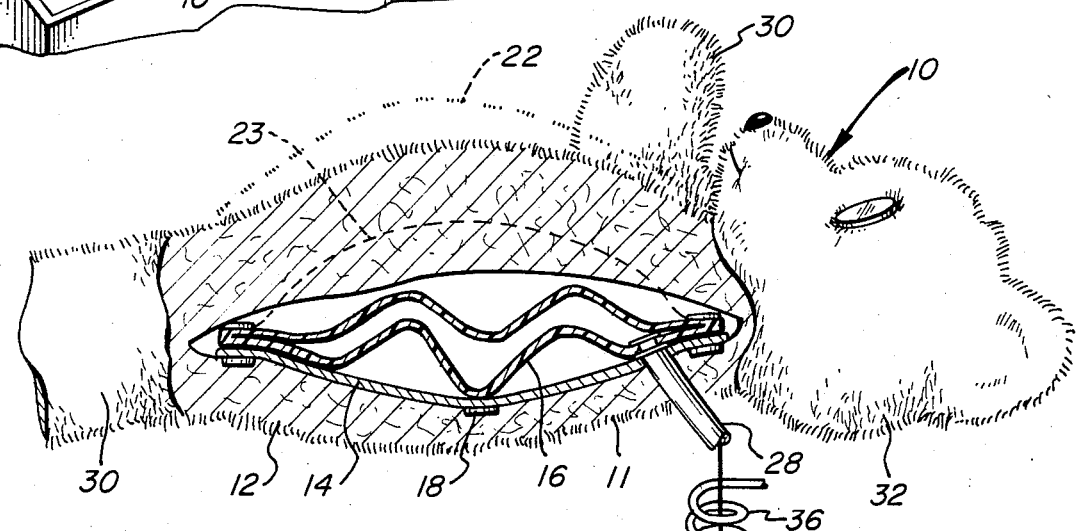
FIG. 2
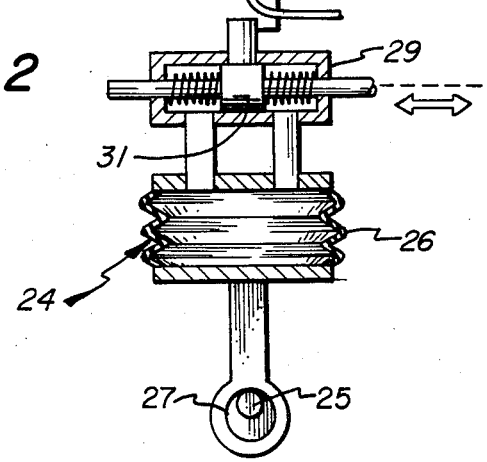

METHOD AND APPARATUS FOR TREATING BREATHING IRREGULARITIES

FIELD OF THE INVENTION

The present invention relates to a method of providing a surrogate mother for a live being. More specifically, it relates to a method of constructing a simulated live animal and a method of simulating a naturally breathing body to pacify a living, mammilian subject or other animal, by positioning such a simulated breathing body, desirably in the form of a toy animal, within the vestibulary (motion sensing) and tactile (touch) vicinity of the subject to comfort it during sleep or rest periods.

BACKGROUND OF THE INVENTION

It has long been known that pacification and sleep inducement of human beings and animals, and particularly human infants and other new-born creatures, are complex psychological and physical phenomena. It is known that either or both vestibular and tactile responses of the subject may be involved, since the sensations of both overt movement and touch, and particularly movement, develop early in gestation of higher animals and are closely associated with birth and early post-partum experiences of the newborn.

It has been customary for years beyond numbers to use dolls, toy animals, "security blankets" and the like, generally having a soft surface or body, to pacify or comfort children.

It is also known, as described in the literature, to provide a pulsed tube of warm water to simulate blood pulse, with or without "weepage" through the tube, to simulate the contact of infant rats with their mother.

However, prior to the present invention there has not been available any simple structure for simultaneously simulating breathing, and accompanying substantial cyclical body movement, of a living being in the form of a toy animal, doll or the like, which may be positioned within the vestibular (motion) and tactile (touch) vicinity of a living subject.

As disclosed in one of my earlier publications, the vestibular response is one of the earliest developed of any of the senses in higher forms of animal life, including humans. In my co-authored article, *Journal of Experimental Child Psychology*, Vol. 10, No. 1, p 6, et seq. August 1970, it is noted that myelinization of vestibular connections are phylogenetically among the earliest in a human fetus. Such myelinization starts at 4 months, is well under way at 6 months, and is quite heavy at term. Such development is in sharp contrast to development of the visual system and the optic nerve which only begins at birth. At the same time, the vestibular control over the movement of the eyes has been demonstrated to already be functional at birth. Accordingly, while it has been known that such vestibular and tactile sensations accompany an infant's contact with its own or a surrogate mother, including siblings, the response only to such vestibular and tactile sensations (without smell, sight and hearing) has not been well understood.

I have found that such vestibular and tactile sensations alone or in combination only with each other have an outstandingly beneficial effect on the reacting creature and by the present invention, these benefits can be achieved exclusively by a mechanical surrogate mother that simulates both breathing movements and the feel of a live being for any creature in its presence.

BRIEF DESCRIPTION OF THE INVENTION

It is a particular object of the present invention to provide a surrogate mother in the form of a mechanically actuatable body that simulates the motions and feel of a live creature to evoke vestibulary and tactile responses of a living subject placed adjacent to or in contact with the body. In accordance with the present invention, sleep irregularities or pacifying of an animal subject are treated by positioning it adjacent to such a simulated body and so that the live being is within touch and motions contact of the body. In a preferred form, the surrogate mother form is that of an animal having a body portion which includes a stiff section, or spine, along a back portion of the trunk and an expandable "pleural cavity" section having its peripheral edge directly connected to it. A plurality of apendages, such as head and legs, are flexibly secured to the trunk portion adjacent such peripheral connection, or interface, between the expandable pleural cavity and the spine section. The pleural cavity section encloses a partially inflatable bladder, with one bladder surface secured to the spine section so that only the front of the outer surface of the pleural cavity undulates outwardly and inwardly when the air pressure in the bladder is varied. The bladder is cyclically inflated to an extent sufficient only to impart motion to the front wall of the trunk, and preferably, but not necessarily, at least some of the appendages simultaneously move relative to the spine section.

In a preferred method of carrying out treatment of sleep irregularities, the bladder is cyclically inflated in a manner to correspond generally with the respiratory rate of the subject in such vestibular or tactile vicinity. In apparatus form, the bladder is inflated by pneumatic pump means which cyclically inflates the bladder through a tube connected through the back. Such inflation is only sufficient to produce external movement of the padded outer surface of the pleural cavity. Desirably the body covering is sheepskin, or has a sheepskin-like deep pile texture, to provide a high nap having air permeability that is sufficient to permit a small animal to imbed its nose into the nap without blocking the nasal passages to air.

Preferably, the bladder may be inflated only sufficiently to substantially, but not completely, fill the pleural cavity of the body portion of the surrogate mother or animal figure, and then the bladder pressure is increased only sufficiently so that it is slightly above atmospheric pressure. Air flows into and out of the bladder through a hose member connected preferably through the back of the figure. It may be mechanically evacuated or the pressure of the atmosphere may partially deflate the bladder between each stroke of the pumping mechanism.

In a rudimentary form the surrogate mother need not have an animal form, but may be in fact a free-form enclosure, having a pair of opposed surfaces with a high nap velvet, or sheepskin-like cover.

Preferably but not necessarily the pump to actuate the bladder of the surrogate mother is positioned some distance away from the animal form, and is driven by an electric motor. An air hose is connected to the pump through the back of the figure to supply compressed air to partially inflate, and if desired, partially deflate the bladder on each cycle. Alternatively of course, the pump mechanism may be embodied within the figure.

In a preferred form the pleural cavity in the torso of the toy animal expands and contracts with as little sound as possible due to incoming and outgoing air expanding and contracting the bladder. Accordingly a foamed plastic material having high air permeability (porous with interconnected air passageways) is formed to fill substantially the pleural cavity and the elastic bladder encloses the foamed plastic as a loose-fitting skin.

Further objects and advantages of the present invention will become apparent from the following detailed description of a preferred embodiment of a surrogate companion and its method of operation to perform the desired functions. The operative features of the invention are described in connection with the accompanying drawings which form an integral part of this specification.

BRIEF DESCRIPTION OF THE DRAWINGS

FIG. 1 is perspective view showing a toy bear constructed in accordance with the present invention in vestibular and tactile proximity to an infant on a bed and indicates the pneumatic pumping mechanism associated therewith.

FIG. 2 is a longitudinal view, partially in cross-section through the trunk of the toy bear and illustrates construction of the animal together with a pneumatic circuit diagram indicating the pumping arrangement for partially inflating the bladder member.

DESCRIPTION OF THE PREFERRED EMBODIMENTS OF THE INVENTION

Figure 3:
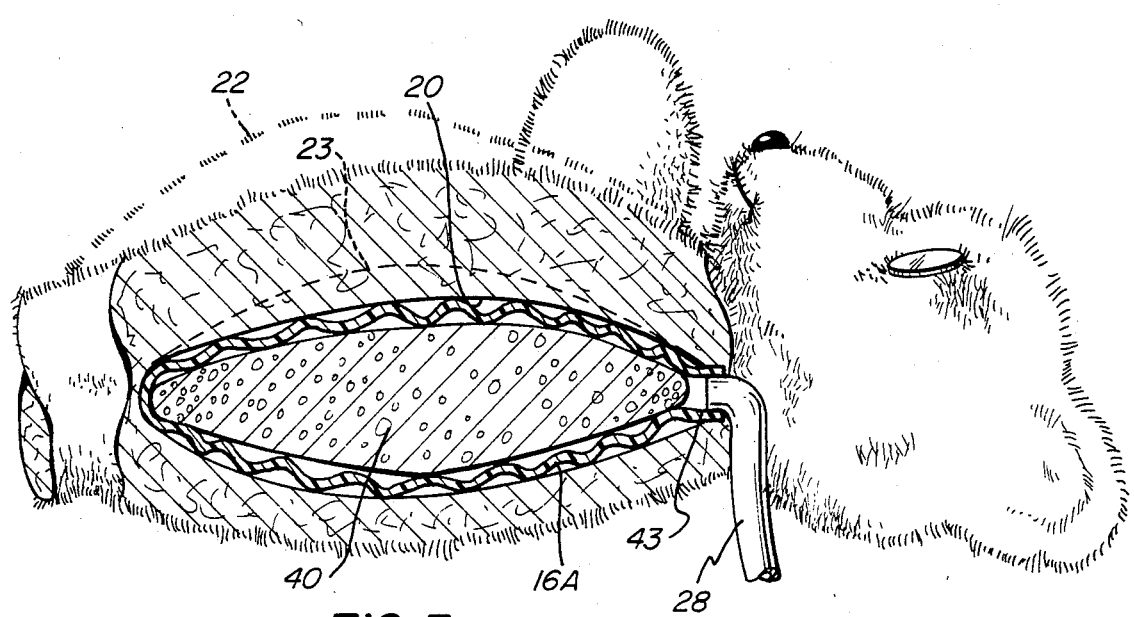
FIG. 3 is a view similar to FIG. 2 illustrating an alternate arrangement of the expandable bladder which encloses a foamed pleural cavity filler.

As indicated in FIG. 1 the method of the present invention is accomplished by positioning a simulation of a cyclically breathing animal, or other figure (surrogate mother), adjacent to the living subject to be treated. In this particular arrangement, the simulated animal is a toy bear 10 whose internal construction is best seen in FIG. 2. As there shown the body portion or trunk 12 is in cross-section illustrating that the lower or back portion 11 includes a stiff section 14 which effectively forms a spine or backbone extending generally across the width of trunk 12. Section 14 forms an anchor for expandable bladder 16 which is secured by plastic clips, such as 18. The attachment may also be by glueing, bonding or other connection so that at least a substantial portion of one side of bladder 16 is firmly anchored against stiff section 14. With bladder 16 so enclosed in "pleural cavity" 20 of toy bear 10, it is thereby possible to simulate actual breathing motions of a live animal, including natural expansion-contraction of the pleural cavity. This produces significant motion of the outer surface, or stomach portion, 22 of trunk 12, as indicated by the dotted lines. Such action is induced by pump mechanism 24 connected through flexible tube 28 to bladder 16.

As indicated, bladder 16 extends along trunk 12 and along spinal section 14 of the toy animal so that its outer periphery is adjacent the interface, or connection, between the appendages such as legs 30 and head 32 to trunk 12. With such positioning of the head and legs, the appendages move relative to the spine portion and at the same time as the upper surface or stomach cover 22 is raised and lowered by inflation and deflation of the bladder. Such movement of the head, or the manipulative or locomotive appendages, of the simulated animal figure permits the animal or human subject under treatment to control the amount of "coupling" it desires with the surrogate mother. Accordingly, there is provided in this way variable tactile and vestibular stimulation to the subject. For example, if toy animal 10 is held closely to the infant, as in FIG. 1, the regular and cyclical movement of the animal figure directly and immediately stimulates both the vestibular and tactile senses of the child. On the other hand if the animal is merely in the vicinity, say in a crib with only a hand, foot or head of the child resting against part of the toy animal, a lesser degree of vestibular response is evoked, but the child still maintains a tactile connection and some motion sensing during continued operation.

Pump mechanism 24 may take any of a number of forms, including as in FIG. 2, bellows 26 acuated by crank shaft 25 through cam member 27 to compress and expand air with each rotation of shaft 25. It has been found that the motor driving the mechanism must be relatively quiet and the mechanical action of the bellows slowly varying to avoid generation of noise. However, the pneumatic, or air, tubing 28 is desirably kept relatively short so that it is convenient to carry with the toy bear. It is particularly important that operation of bellows 26 be smooth and regular so that changes in pressure cannot be felt or heard as air moves into and out of bladder 16 and consequently there are no sharp impulses generated within the toy animal. Desirably, but not necessarily, bladder 16 may be inflated to a point just slightly above atmospheric pressure so that upon expansion into a distended condition as indicated by dotted line 23, the front surface covering 22 over pleural cavity 20 remains soft and pliable even when so expanded. However, there is still sufficient resiliency in expanded bladder 16 so that upon opening the return passage through line 28, by movement of piston 31 in slide valve 29, air may exhaust slowly and smoothly due to its pressure difference from atmospheric pressure and the elasticity of bladder 16. In the present instance bladder 16 is shown to be formed of a blood pressure cuff. Such a structure is particularly adapted to provide a considerable range of motion to surface 22, with only a slight increase in pressure above atmospheric.

FIG. 3 indicates a modification of the bladder for simulated breathing motion that has been formed to be particularly effective where extraneous sounds are objectionable. For example, in isolettes used for care of premature babies the sounds of air entering and leaving bladder 16 appear to be amplified in such a confined space. Further, such sound of air moving may also be accompanied by sudden additional sound created by changes in shape of bladder 16 within the torso.

As particularly shown in FIG. 3, a light weight foam rubber or plastic material having high permeability to air flow has been found to be suitable to suppress or substantially eliminate both of such noise sources when loosely enclosed within bladder 16A. A material adequate for such purposes, (high air permeability) is presently marketed by Parker Bros. of Beverly, Mass. under the registered trademark "NERF" foam ball. I have found that such structure can be created by forming foam material 40 to approximate the shape and volume of hollow pleural cavity 20 to dotted line 23. Bladder 16A is then formed to cover foam body 40 like a loose skin when uninflated. Thus bladder 16A is generally held against the inner surface of the pleural cavity.

Figure 4:
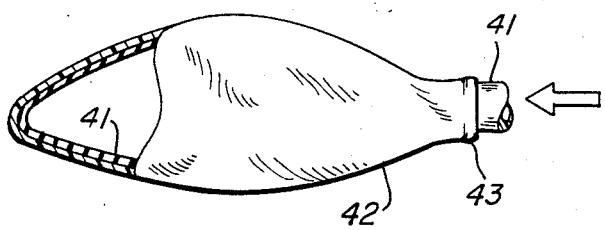
FIGS. 4, 5, 6 and 7, each partially in cross-section illustrate successive steps in forming the bladder and the enclosed porous foam unit.
Figure 5:
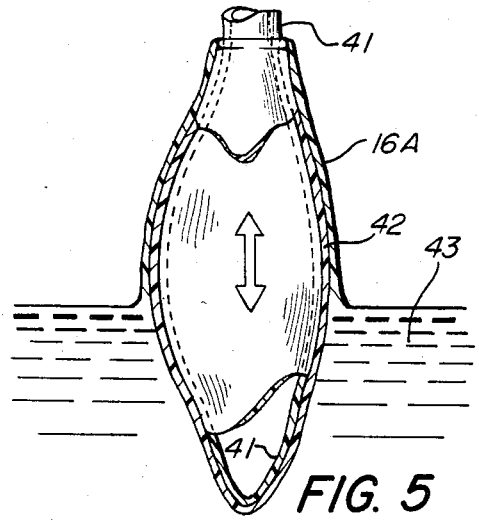
Figure 6:
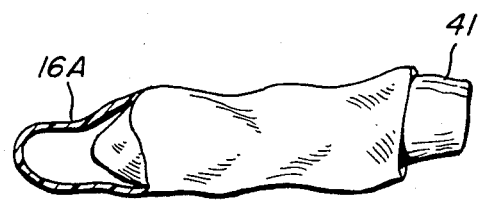
Figure 7:
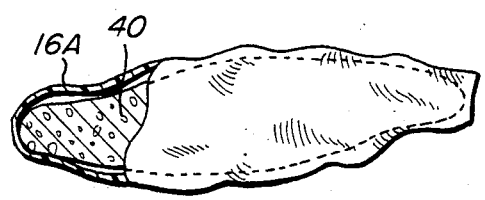

Desirably, the bladder 16A may be molded of liquid latex. One satisfactory method for so forming bladder 16A is illustrated in FIGS. 4 to 7. As shown in FIG. 4, a balloon 41 is inflated to approximate the correct size. Balloon 41 is sprayed with a coating 42 of silicone, or other release material. The coated balloon is then dipped, as indicated in FIG. 5, in liquid latex 43 to form bladder 16A. The neck 43 of balloon 41 is slightly enlarged to accept formed foam ball 40 before the latex bladder dries. After removal and drying, balloon 41 may be stripped out of the bladder 16A as indicated in FIG. 6, and then body 40 inserted as shown in FIG. 7. The air hose is then enclosed by neck 43 to complete the inflatable bladder as seen in FIG. 3.

While the present embodiment as indicated above is shown in the form of a toy animal, it will be understood that any form of figure including a free-form pillow enclosure may be provided with a sheepskin or deep plush pile to cover a pair of opposed sheet surfaces forming a generally inflatable body. To accentuate simulated breathing of such a body, of course, where the bladder is not foam filled as above noted at least one surface is preferably made relatively stiff. Thus, motion of the opposite surface is amplified relative to the back surface. Accordingly at least one of the sheet members is inflatable and either formed integral with the stiff surface or a separate bladder member, with one surface relatively inflexible, and not susceptible to lateral expansion. Where the body is foam filled, as in FIG. 3 the motion of free surface 22 does not require a stiff support on the opposite surface.

It may be desirable under certain circumstances to warm the air that is supplied to the inflatable member. Such warmth may be added by a hot water heat source, such as coil 36 around tube 28. Air may be recirculated continuously in and out of bladder 16, or it may flow through bladder 16 by providing a small relief hole (not shown) in the bladder. This permits a certain amount of air to bleed continuously out of the inflatable member.

While only a few embodiments of the present invention have been disclosed it will of course be apparent to those skilled in the art that the method of treating a live being in accordance with the present invention, as well as the method of assembly and maufacture of the structure to simulate a living animal may be made without departing from the teachings of this invention. All such modifications and changes coming within the scope of the following claims are intended to be included.

I claim:

1. Apparatus for simulating natural breathing motions of a live subject which comprises a simulated animal adapted to be positioned within the immediate vicinity of such a live subject, said simulated animal having a torso including a back portion and a front portion, said portions being peripherally joined and enclosing an inflatable bladder member to simulate lungs of said simulated animal within its pleural cavity section formed between said back and front portions, said back portion being substantially stiffer across the area of said baldder member than said front portion, and said front portion being easily flexible, a plurality of appendages to simulate a head and manipulative or locomotive means, each of said appendages being flexibly connected to said torso adjacent the periphery of said bladder member, and air pump means for cyclically inflating said bladder member sufficiently to produce movement of the external surface of said front portion of said pleural cavity section relative to said back portion and to move at least one of said appendages to simulate motion accompanying a natural breathing pattern for said simulated animal, said pattern being relatable to the vestibular and tactile senses of said live subject, said air pump including means for heating the air supplied to said bladder, said bladder member including means permitting the air to bleed through the wall thereof.

2. Apparatus in accordance with claim 1 wherein at least a substantial portion of one side of said bladder member is firmly anchored against said stiffer portion.

3. Apparatus in accordance with claim 1 wherein said means permitting the air to bleed through said bladder wall includes a relief opening to permit flow of a portion of the air therefrom upon inflation.

4. Apparatus in accordance with claim 1 wherein said bladder encloses an air-permeable unit generally conforming to the surface of said bladder member before inflation to suppress sound transmission through air pumped into said bladder member.

5. A method for providing rhythmic stimulation which is biologically appropriate for treating respiration and sleep irregularities of a mammalian subject which comprises positioning a simulation of a live being in an environment conductive to sleeping in sufficiently close physical proximity to said subject to place it within easy reach of said subject, said simulation including a torso portion having a relatively stiff section along one side thereof and a relatively soft and flexible section along the other side thereof, said stiff and flexible sections being joined about their peripheries to form, respectively, the back and front walls of a variable-volume, expandable, pleural cavity in said torso portion, a plurality of appendages including a head and manipulative members flexibly secured to said torso portion at the peripheral edges of said expandable pleural cavity and a partially inflatable, expandable bladder enclosed within said pleural cavity, one surface portion of said bladder being in movement-resistive contact with said stiff section and an expandable surface of said bladder in contact with the front wall of said pleural cavity, and cyclicially inflating and deflating said bladder to an extent to impart external motion to the front wall of said torso portion and accompanying motion to said appendages relative to said stiff section controlling, such cyclical inflating and deflating to approximate respiratory movements at the rate of breathing of said subject, whereby the regular cyclicity of the movements of the device will tend to increase regularity of cyclicity in the breathing of the subject.

6. A method for providing rhythmic stimulation which is biologically appropriate for pacifying a live subject which comprises positioning a simulation of a breathing animal, in an environment conductive to rest, within sufficiently close physical proximity of a subject to allow said subject to readily attain physical contact with the simulation, said simulation having a body portion including a broad spinal section along the simulated back of a torso portion, a flexible, expandable front wall section along the front of said torso portion directly opposed to said spinal section, said sections being peripherally joined one to the other at an interface to form an expandable pleural cavity section, a simulated head and a plurality of manipulative appendages flexibly secured to said torso portion adjacent said interface, said pleural cavity section having a partially inflatable bladder member enclosed therein with one surface portion of said bladder member in movement-resistive contact with said spine section and the opposite surface portion thereof being in expandable contact with the inner surface of said front wall section, and cyclically inflating and deflating said bladder member to an extent to substantially displace the front wall section of said torso relative to said spinal section, the inflation of said bladder being sufficient to cause motion of said appendages relative to said spinal section to simulate respiratory motions of an animal in the immediate vicinty of the subject to be pacified.

* * * * *